(12) United States Patent
Koenemann

(10) Patent No.: US 8,038,681 B2
(45) Date of Patent: Oct. 18, 2011

(54) MODULAR FEMORAL ORTHOPAEDIC SURGICAL INSTRUMENT

(75) Inventor: Jeffery L. Koenemann, Plymouth, IN (US)

(73) Assignee: DePuy Products, Inc., Warsaw, IN (US)

( * ) Notice: Subject to any disclaimer, the term of this patent is extended or adjusted under 35 U.S.C. 154(b) by 1052 days.

(21) Appl. No.: 11/865,022

(22) Filed: Sep. 30, 2007

(65) Prior Publication Data

US 2009/0088762 A1    Apr. 2, 2009

(51) Int. Cl.
*A61B 17/58* (2006.01)

(52) U.S. Cl. .......................................... 606/88

(58) Field of Classification Search ................ 606/88
See application file for complete search history.

(56) References Cited

U.S. PATENT DOCUMENTS

| | | | |
|---|---|---|---|
| 5,258,032 A | 11/1993 | Bertin | |
| 5,458,645 A | 10/1995 | Bertin | |
| 5,624,444 A * | 4/1997 | Wixon et al. | 606/88 |
| 5,683,397 A * | 11/1997 | Vendrely et al. | 606/88 |
| 5,683,472 A * | 11/1997 | O'Neil et al. | 623/20.31 |
| 5,702,460 A | 12/1997 | Carls et al. | |
| 5,716,361 A | 2/1998 | Masini | |
| 5,879,393 A | 3/1999 | Whiteside et al. | |
| 5,885,296 A | 3/1999 | Masini | |
| 5,944,722 A | 8/1999 | Masini | |
| 5,947,973 A | 9/1999 | Masini | |
| 5,957,926 A | 9/1999 | Masini | |
| 5,961,523 A | 10/1999 | Masini | |
| 5,971,989 A | 10/1999 | Masini | |
| 6,068,633 A | 5/2000 | Masini | |
| 6,077,269 A | 6/2000 | Masini | |
| 6,080,196 A | 6/2000 | Bertin | |
| 6,102,916 A | 8/2000 | Masini | |
| 6,187,010 B1 | 2/2001 | Masini | |
| 6,214,011 B1 | 4/2001 | Masini | |
| 6,575,980 B1 | 6/2003 | Robie et al. | |
| 7,128,745 B2 | 10/2006 | Masisni | |
| 2004/0039450 A1 | 2/2004 | Griner et al. | |
| 2004/0153087 A1 | 8/2004 | Sanford et al. | |
| 2005/0107884 A1 * | 5/2005 | Johnson et al. | 623/20.15 |
| 2006/0200162 A1 | 9/2006 | Farling et al. | |

FOREIGN PATENT DOCUMENTS

EP    0914806    5/1999
FR    2867056    9/2005

OTHER PUBLICATIONS

European Search Report for European Patent Application No. 2042111A3, Mar. 11, 2010, 3 pgs.

* cited by examiner

*Primary Examiner* — Nicholas Woodall
(74) *Attorney, Agent, or Firm* — Barnes & Thornburg LLP

(57) ABSTRACT

A femoral orthopaedic surgical instrument includes a posterior femoral trial having a cutting guide defined therein and an anterior femoral trial removably coupled to the posterior femoral trial. The anterior femoral trial may also include a cutting guide defined therein. The femoral orthopaedic surgical instrument may also include a base block couplable to the posterior femoral trial in place of the anterior femoral trial. A plurality of additional orthopaedic instruments may be coupled to the base block.

16 Claims, 7 Drawing Sheets

MODULAR FEMORAL ORTHOPAEDIC SURGICAL INSTRUMENT

TECHNICAL FIELD

The present disclosure relates generally to orthopaedic prostheses, and particularly to a femoral joint prostheses for a knee replacement surgery.

BACKGROUND

Joint arthroplasty is a well-known surgical procedure by which a diseased and/or damaged natural joint is replaced by a prosthetic joint. A typical knee prosthesis includes a tibial tray, a femoral component, and a polymer insert or bearing positioned between the tibial tray and the femoral component. The femoral component generally includes a pair of spaced apart condylar portions, the surfaces of which articulate with corresponding surfaces of the polymer bearing.

The femoral component is configured to be coupled to a surgically-prepared distal end of a patient's femur. The femur is surgically-prepared during an orthopaedic surgical procedure performed by an orthopaedic surgeon. During the orthopaedic surgical procedure, the orthopaedic surgeon typically uses a number of separate orthopaedic surgical instruments such as, for example, a femoral anterior cutting block, an femoral augment cutting block, and a femoral trial.

SUMMARY

According to one aspect, a femoral orthopaedic surgical instrument may include a posterior femoral trial, an anterior femoral trial, and a base block. The posterior femoral trial and the anterior femoral trial may each include a cutting guide defined therein. For example, the posterior femoral trial may include a first cutting guide, a second cutting guide spaced from the first cutting guide by a first distance, and a third cutting guide spaced from the second cutting guide by the first distance. Additionally or alternatively, the posterior femoral trial may include distal cutting guide and a posterior cutting guide.

The base block may be removably coupled to the posterior femoral trial. Additionally, the base block may be configured to be coupled to a femur of a patient. The anterior femoral trial may be configured to be coupled to the posterior femoral trial in place of the base block.

In some embodiments, the femoral orthopaedic surgical instrument may include a bushing coupled to the base block. For example, the bushing may be received in an opening of the base block. Additionally, in some embodiments, the femoral orthopaedic surgical instrument may include an intramedullary rod, which may be received in an aperture of the bushing. In some embodiments, the bushing may include a frame and a bushing insert. The frame may be received in the opening of the base block. The bushing insert may be received in the frame. Additionally, the bushing insert may include an aperture defined therein configured to receive an orthopaedic surgical instrument. The femoral orthopaedic surgical instrument may also include a stylus coupled to the base block.

In some embodiments, the femoral orthopaedic surgical instrument may include a box cutting guide. The box cutting guide may be coupled to the anterior femoral trial. In some embodiments, the box cutting guide may be embodied as a platform having a first peg and a second peg extending therefrom. In such embodiments, the anterior femoral trial may include a first aperture and a second aperture. The first peg may be received in the first aperture and the second peg may be received in the second aperture.

Additionally, in some embodiments, the femoral orthopaedic surgical instrument may include a femoral box trial configured to be coupled to the anterior femoral trial and the posterior femoral trial. For example, the anterior femoral trial may include a first slot and second slot and the posterior femoral trial may include a third slot and fourth slot. In such embodiments, the femoral box trial may include a first rail and a second rail. The first rail of the femoral box trial may receive in the first slot and the third slot and the second rail may be received in the second slot and the fourth slot when the femoral box trial is coupled to the anterior femoral trial and the posterior femoral trial. In some embodiments, the femoral anterior trial and the femoral posterior trial define an aperture therebeween when coupled together. In such embodiments, the femoral box trial may be received in the aperture. Additionally, in some embodiments, the femoral orthopaedic surgical instrument may include a stem configured to be coupled to the femoral box trial.

According to another aspect, a modular femoral trial may include a posterior femoral trial and an anterior femoral trial separate from the posterior femoral trial. The anterior femoral trial may be removably coupled to the posterior femoral trial. The posterior femoral trial may include a first cutting guide defined therein. The anterior femoral trial may include a second cutting guide defined therein. In some embodiments, the modular femoral trial may also include a femoral box trial coupled to the anterior femoral trial and the posterior femoral trial. Additionally, in some embodiments, the femoral anterior trial and the femoral posterior trial may define an aperture therebeween. In such embodiments, the femoral box trial may be received in the aperture.

In some embodiments, the anterior femoral trial may include a first slot and second slot. Additionally, the posterior femoral trial may include a third slot and a fourth slot. In such embodiments, the femoral box trial may include a first rail received in the first slot and the third slot and a second rail received in the second slot and the fourth slot.

In some embodiments, the modular femoral trial may also include a base block configured to be coupled to the posterior femoral trial in place of the anterior femoral trial. The base block may include a plurality of guide pin apertures. Additionally, the posterior femoral trial may include a distal cutting guide and a posterior cutting guide. Further, in some embodiments, the modular femoral trial may include a box cutting guide coupled to the anterior femoral trial. The box cutting guide may include a first peg and a second peg. In such embodiments, the anterior femoral trial may include a first aperture and a second aperture. The first peg may be received in the first aperture and the second peg may be received in the second aperture.

According to a further aspect, a method for performing an orthopaedic surgical procedure may include coupling a posterior femoral trial having a cutting guide defined therein with a base block. The method may also include resectioning a patient's femur using the cutting guide of the posterior femoral trial. Additionally, the method may include removing the base block from the posterior femoral trial and coupling an anterior femoral trial having a cutting guide to the posterior femoral trial. The method may additionally include resectioning the patient's femur using the cutting guide of the anterior femoral trial.

BRIEF DESCRIPTION OF THE DRAWINGS

The detailed description particularly refers to the following figures, in which.

DETAILED DESCRIPTION OF THE DRAWINGS

Figure 1:
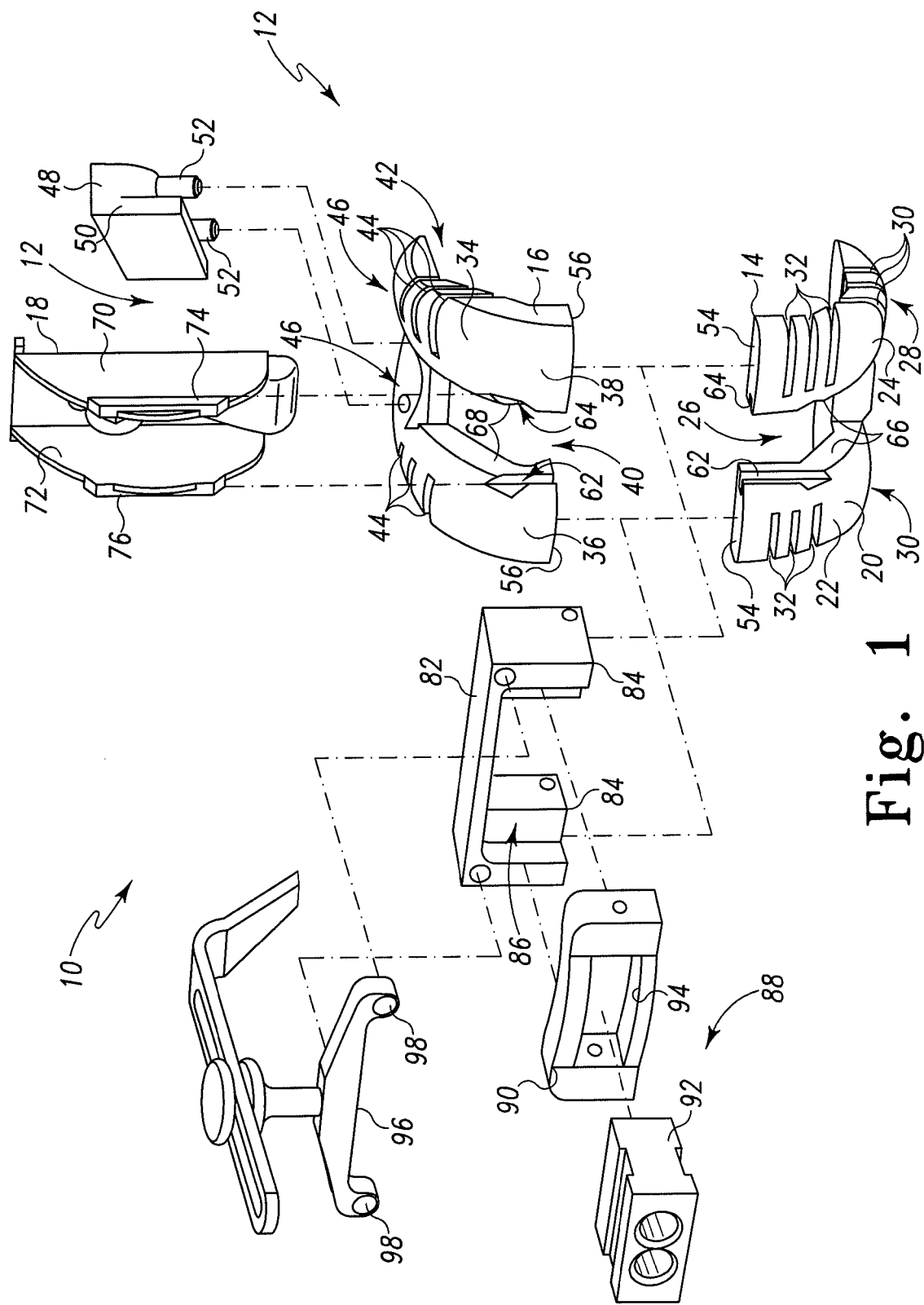
FIG. 1 is an exploded view of various components of a modular femoral orthopaedic surgical instrument.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Referring to FIG. 1, an orthopaedic surgical instrument 10 for use on a femur of a patient includes a modular femoral trial 12. The modular femoral trial 12 includes a posterior femoral trial 14, an anterior femoral trial 16, and a femoral box trial 18. The posterior femoral trial 14, the anterior femoral trial 16, and the femoral box trial 18 are configured to be removably coupled to each other as discussed in more detail below. The trials 14, 16, 18 may be formed from an implantable metal such as stainless steel or cobalt chrome.

The posterior femoral trial 14 includes an articulating surface 20 configured to contact a natural or prosthetic upper bearing surface of the patient's tibia. The articulating surface 20 includes a pair of condylar surfaces 22, 24 spaced apart to form an opening 26 therebetween. The posterior femoral trial 14 also includes a number of cutting guides 28, which may be used during an orthopaedic surgical procedure to resect a portion of a patient's femur. For example, the posterior femoral trial 14 may include a number of distal cutting guides 30 and a number of posterior cutting guides 32. In the illustrative embodiment, the posterior femoral trial 14 includes three distal cutting guides 30 and three posterior cutting guides 32. The illustrative cutting guides 28 are embodied as elongated openings configured to receive a bone saw blade of an orthopaedic bone saw or other cutting device. The distal cutting guides 30 may be used by an orthopaedic surgeon to facilitate the resection of a portion of the distal end of a patient's femur. Similarly, the posterior cutting guides 32 may be used by the orthopaedic surgeon to facilitate the resection of a portion of the posterior condyles of the patient's femur.

Each of the cutting guides of the distal cutting guides 30 and the posterior cutting guides 32 are spaced apart from each respective cutting guide 30, 32 a fixed distance. For example, the distal cutting guides 30 may be spaced apart from each other about two millimeters. Similarly, the posterior cutting guides 32 may be spaced apart from each other about two millimeters. As such, during the orthopaedic surgical procedure, the surgeon may select the particular cutting guide 30, 32 to use to remove the desired amount of bone. In other embodiments, the posterior femoral trial 14 may include any number of cutting guides 22, which may be spaced apart by an amount less or greater than two millimeters.

Similar to the posterior femoral trial 14, the anterior femoral trial 16 includes an articulating surface 34 configured to contact a natural or prosthetic upper bearing surface of the patient's tibia and/or a natural or prosthetic surface of the patient's patella. The articulating surface 34 includes a pair of condylar surfaces 36, 38 spaced apart to form an opening 40 therebetween. The anterior femoral trial 16 also includes a number of cutting guides 42. The cutting guides 42 are illustrative embodied as distal cutting guides 44, but may be defined in the anterior femoral trial as other types of cutting guides in other embodiments.

The anterior femoral trial 16 also includes a pair of apertures 46 defined in the articulating surface 34 toward the anterior end of the trial 16. The apertures 32 are configured to receive posts or pegs of various orthopaedic surgical tools usable by an orthopaedic surgeon during an orthopaedic surgical procedure as discussed in more detail below. For example, a box cut guide 48 may be coupled to the anterior femoral trial 16 via the apertures 46. That is, the box cut guide 48 includes a cutting guide platform 50 and a pair of pegs 52, which extend downwardly from the platform 50 as illustrated in FIG. 1. The pegs 52 are sized and positioned on the platform 50 such that the pegs 52 are received in the apertures 46 of the anterior femoral trial 16 when the box cutting guide 48 is coupled thereto as discussed in more detail below in regard to process step 110 of algorithm 100.

As discussed above, the posterior femoral trial 14 and the anterior femoral trial 16 are configured to be coupled together. As such, the posterior femoral trial 14 includes a pair of end surfaces 54 that confront or abut a corresponding pair of end surfaces 56 of the anterior femoral trial 16. The trials 14, 16 may be coupled together using any suitable securing devices. For example, the trials 14, 16 may be coupled together using a number of pins, screws, bolts, or the like. When the trials 14, 16 are coupled together, the openings 26, 40 of the respective rails 14, 16 form an opening 60 (see FIG. 5) configured to receive a portion of the femoral box trial 18 as discussed below. The posterior femoral trial 14 and the anterior femoral trial 16 include corresponding tracks or slots 62, 64 defined in inner sidewalls 66, 68, respectively. When the trials 14, 16 are coupled together, the tracks 62, 64 are abutted to each other.

After the trials 14, 16 are coupled to each other, the femoral box trial 18 may be coupled to the trials 14, 16. The femoral box trial 18 includes two side walls 70, 72. Each of the sidewalls 70, 72 includes a corresponding rail 74, 76. The femoral box trial 18 may be coupled to the posterior and anterior trials 14, 16 by positioning the femoral box 18 such that the rails 74, 76 are received in the corresponding tracks 62, 64. In some embodiments, a stem 80 (see FIG. 7) may be coupled to the femoral box trial using bolt or other securing device 82.

As discussed in more detail below, a base block 82 may be coupled to the posterior femoral trial 14 in place of the anterior femoral trial 16 during the orthopaedic surgical procedure. Similar to the anterior femoral trial 16, the base block 82 includes a pair of ends 84 configured to confront or abut the ends 54 of the posterior femoral trial 14. The base block 82 and the posterior femoral trial 14 may be coupled together using any suitable securing devices such as pins, screws, bolts, or the like. The base block 82 is also configured to be secured to the patient's femur during the orthopaedic surgical procedure. As such, the base block 82 may include a number of apertures for receiving guide pins therein to secure the box 82 to the femur.

The base block 82 forms an attachment base to which a number of different orthopaedic surgical tools or instruments may be coupled. For example, the base block 82 illustratively includes a recess 86 configured to receive a bushing 88. The bushing 88 includes a frame 90 and a bushing insert 92. The frame 90 is configured to be received in the recess 86 of the base block 82 and includes an aperture 94 configured to receive the bushing insert 92. The illustrative bushing insert 92 is a intramedullary bushing configured to receive an intramedullary rod. However, in other embodiments the bushing insert 92 may be embodied as or replaced with a drill bushing. In addition to the bushing 88, a stylus 96 may be coupled to the base block 82. The stylus 96 includes a number of pin guides 98, which are sized and position to match the pin guides of the base block 82.

It should be appreciated that orthopaedic surgical instrument 10 is a modular instrument that may be assembled in one of a number of configurations. For example, the instrument 10 may be initially configured as a resectioning guide or tool. Over the course of an orthopaedic surgical procedure, the instrument 10 may be configured as a femoral trial as discussed in more detail below. As such, an orthopaedic surgeon may perform resectioning of the patient's femur, trial reduction, and analyze the trial range of motion using the instrument 10.

Figure 2:
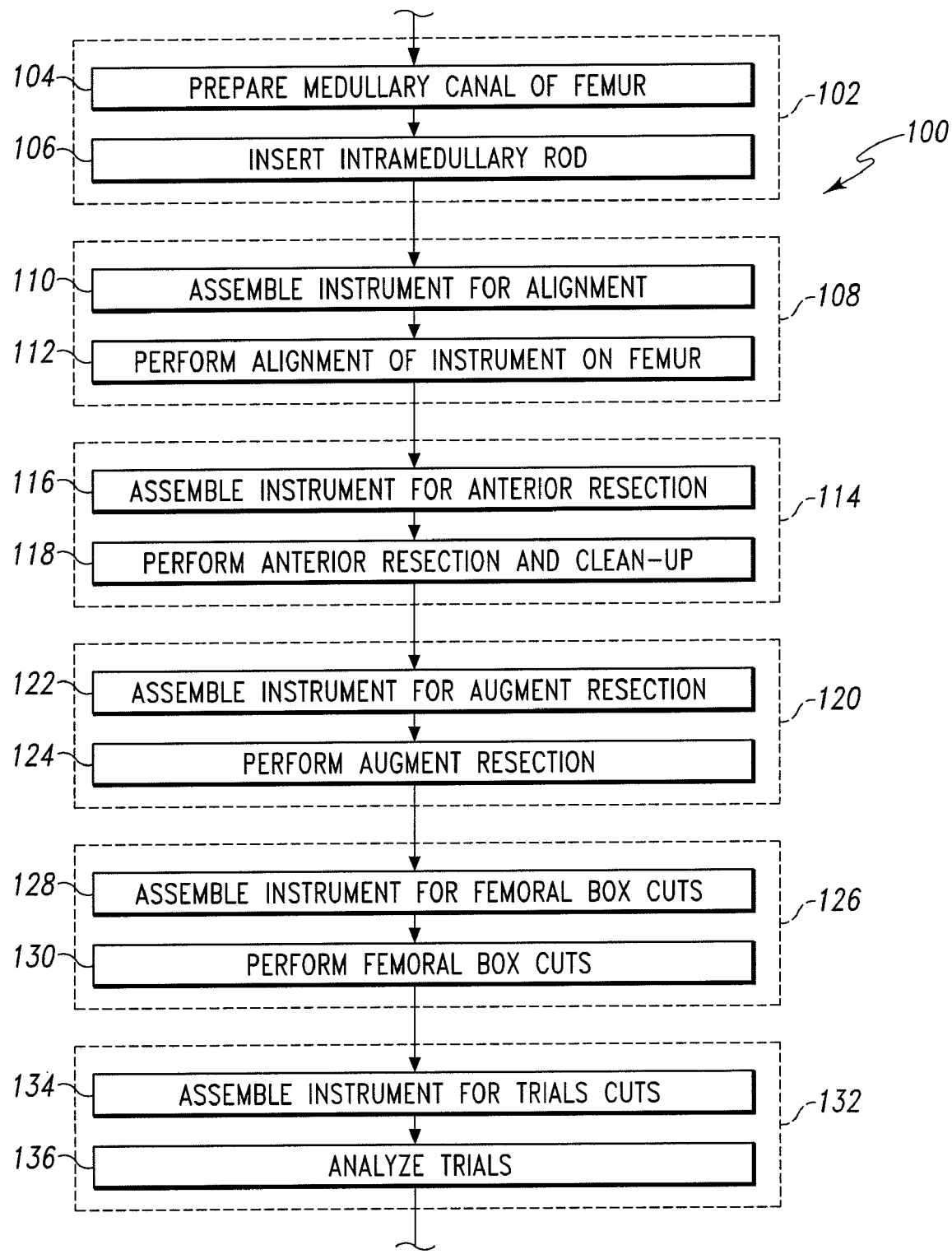
FIG. 2 is a simplified flow diagram of an algorithm for preparing a femur of a patient for a femoral prosthesis using the modular femoral orthopaedic surgical instrument of FIG. 1.

Referring now to FIG. 2, the orthopaedic surgical instrument 10 may be used in an orthopaedic surgical procedure 100 for preparing a patient's femur for an orthopaedic implant. It should be appreciated that the surgical procedure 100 and the instrument 10 are described herein in reference to an orthopaedic revision knee surgical procedure but may be used in a primary knee surgical procedure in other embodiments.

The orthopaedic procedure 100 beings with a process step 102 in which the patient's femur 200 is initially prepared. For example, in process step 104 the medullary canal of the patient's femur 200 is prepared. To do so, the orthopaedic surgeon may drill and ream the medullary canal to define a cavity in the patient's femur 200. Once the cavity is sufficiently defined, the orthopaedic surgeon may insert an intramedullary rod 202 into the cavity defined in the medullary canal of the patient's femur 200. In some embodiments, the rod 202 includes or is coupled to a stem trial 204, which is inserted into the prepared medullary canal (see, e.g., FIG. 3).

Figure 3:
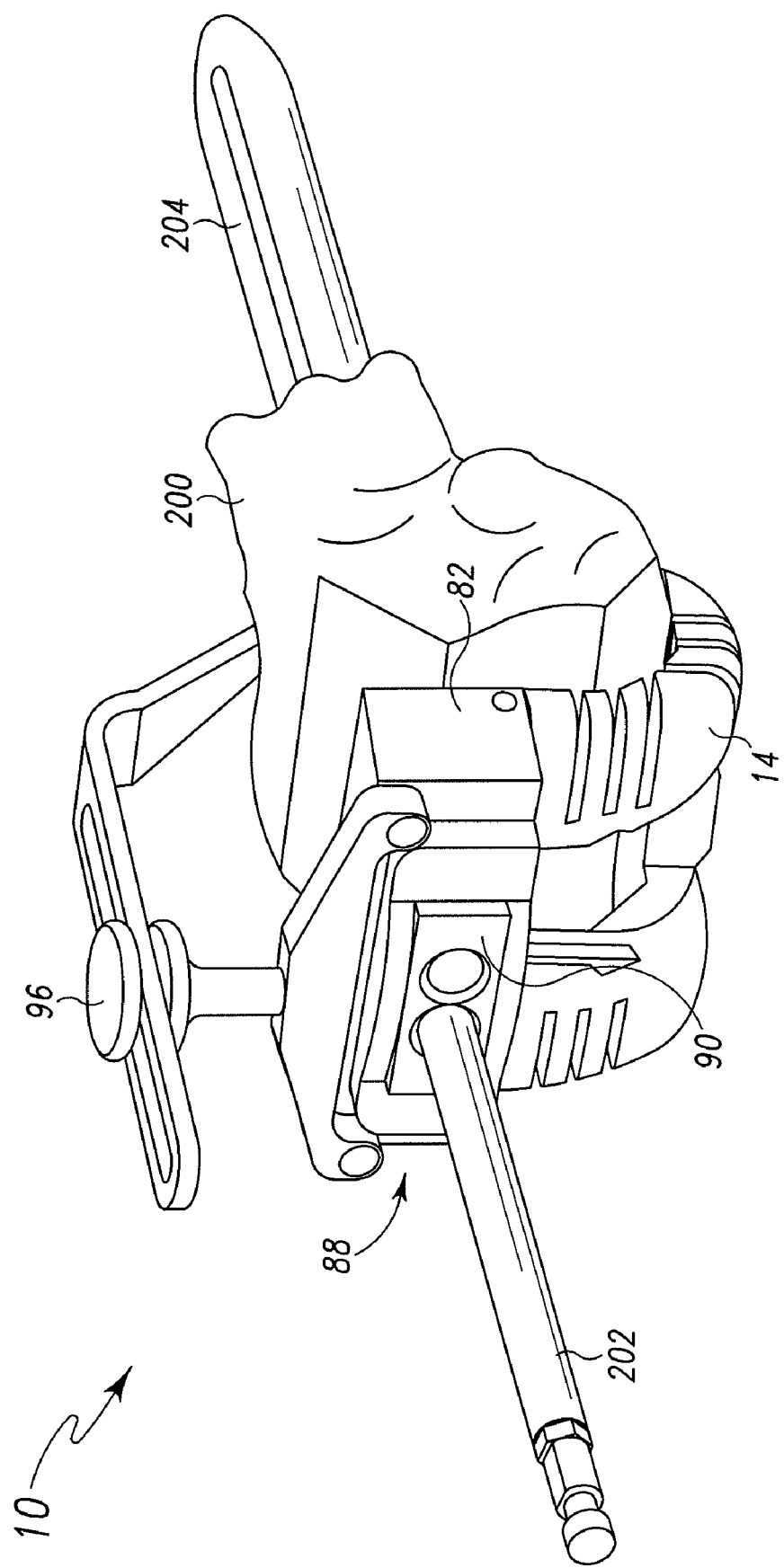
FIG. 3 is a perspective view of one configuration of the modular femoral orthopaedic surgical instrument of FIG. 1 coupled to a femur of a patient.

After the intramedullary rod 202 is inserted into the patient's femur 200, the instrument 100 may be secured and aligned to the patient's femur 200 in process step 108. To do so, the orthopaedic surgeon assembles the instrument 10 in a configuration for alignment of the instrument 10 in process step 110. For example, as illustrated in FIG. 3, the orthopaedic surgeon couples the posterior femoral trial 14 to the base block 82. Additionally, the bushing 88 is coupled to the base block 82. In the illustrative embodiment, the bushing 88 includes a bushing insert 92 configured for intramedullary rods, but in other embodiments or steps, the bushing insert 92 may be replaced with a drill bushing or the like.

After the instrument 10 has been assembled into the alignment configuration, the instrument 10 may be coupled to the intramedullary rod 202, which was inserted in the patient's femur 200 in process step 106. To do so, the intramedullary rod 202 is inserted into the intramedullary rod bushing insert 92. The instrument 10 may then be moved down the rod 202 to the femur 200 in a position for alignment. It should be appreciated that because the instrument 10 includes the posterior femoral trial 14, the instrument 10 may also be used for flexion gap balancing in the alignment configuration illustrated in FIG. 3.

In process step 112, the orthopaedic surgical instrument 10 is aligned with respect to the intramedullary rod 202 and the patient's femur 200. To do so, the position of the instrument 10 is adjusted such that the stylus 96 indicates on or contacts the anterior cortex of the patient's femur 200 so that the sizing of the orthopaedic prosthesis may be accomplished. After the instrument 10 has been properly aligned, the instrument 10 may be secured to the patient's femur 200 in some embodiments. To do so, the base block 82 may be secured to the femur 200 using guide pins or the like.

Figure 4:
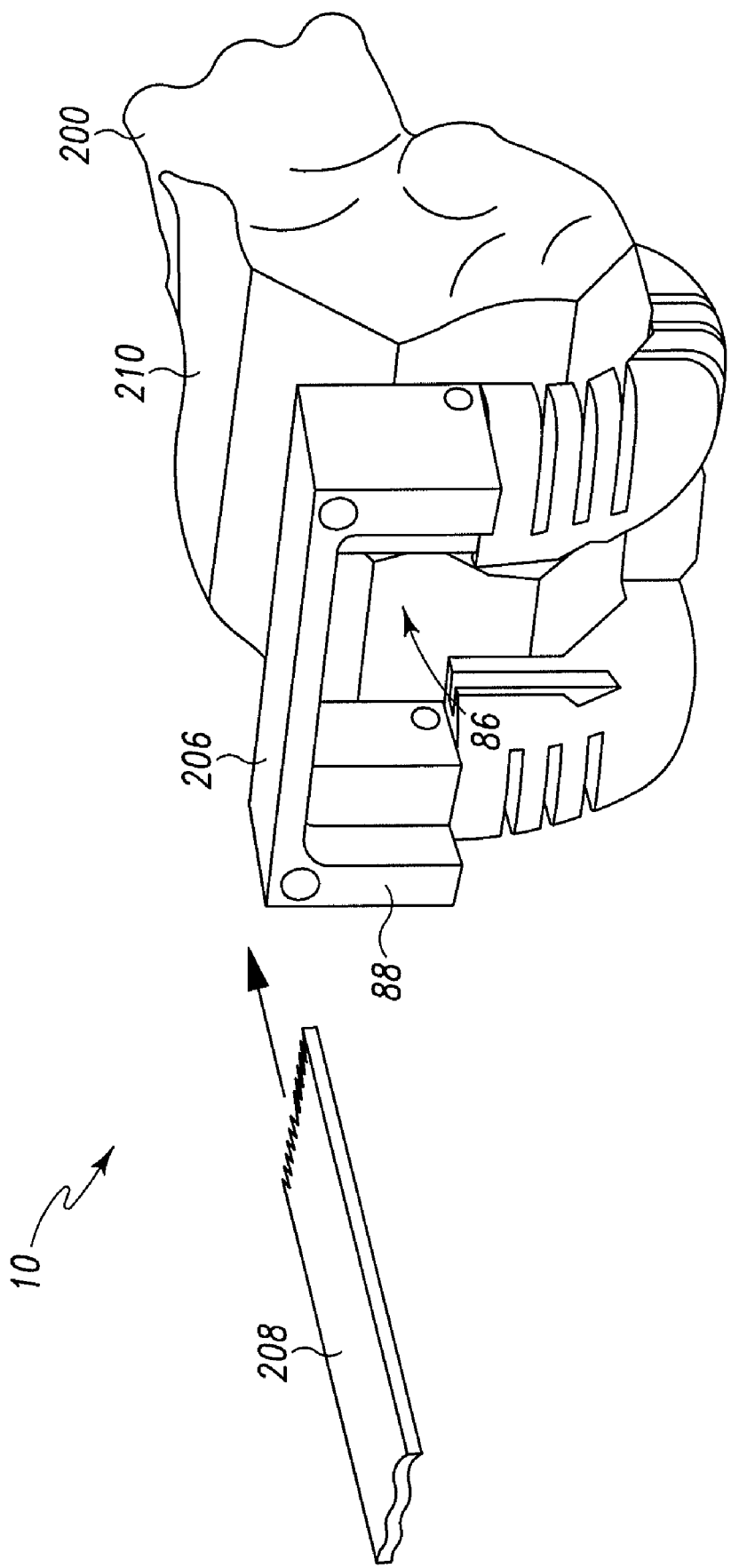
FIG. 4 is a perspective view of another configuration of the modular femoral orthopaedic surgical instrument of FIG. 1 coupled to a femur of a patient.

After the instrument 10 has been aligned, the orthopaedic surgeon may begin resecting the patient's femur 200. For example, the surgeon may perform an anterior resection in process step 114 using the instrument 10. For example, in process step 116, the orthopaedic surgeon assembles the instrument 10 for anterior resection. To do so, as illustrated in FIG. 4, the bushing 88 and the stylus 96 are removed from the base block 82. The base block 82 may then be used as a cutting guide block. That is, a top surface 206 of the base block 82 may be used as a cutting guide. It should be appreciated that the top surface 206 forms a non-captured or open cutting guide.

In process step 118, the surgeon performs the anterior resection of the patient's femur 200. To do so, the surgeon uses the top surface 206 to guide a bone saw blade 208 of an orthopaedic bone saw. The bone saw blade 208 is typically kept substantially flat on the surface 206 to perform the anterior cut. As illustrated in FIG. 4, the anterior cut removes an anterior portion of the patient's femur 200 to create a substantial planar anterior surface 208. In addition to the anterior resectioning of the patient's femur, the surgeon may perform any required broaching. That is, because the bushing 88 has been removed from the base block 82, the distal end of the femur 200 is accessible through the base block 82. As such, the orthopaedic surgeon may perform additional drilling or reaming on the distal end of the femur 200.

Figure 5:
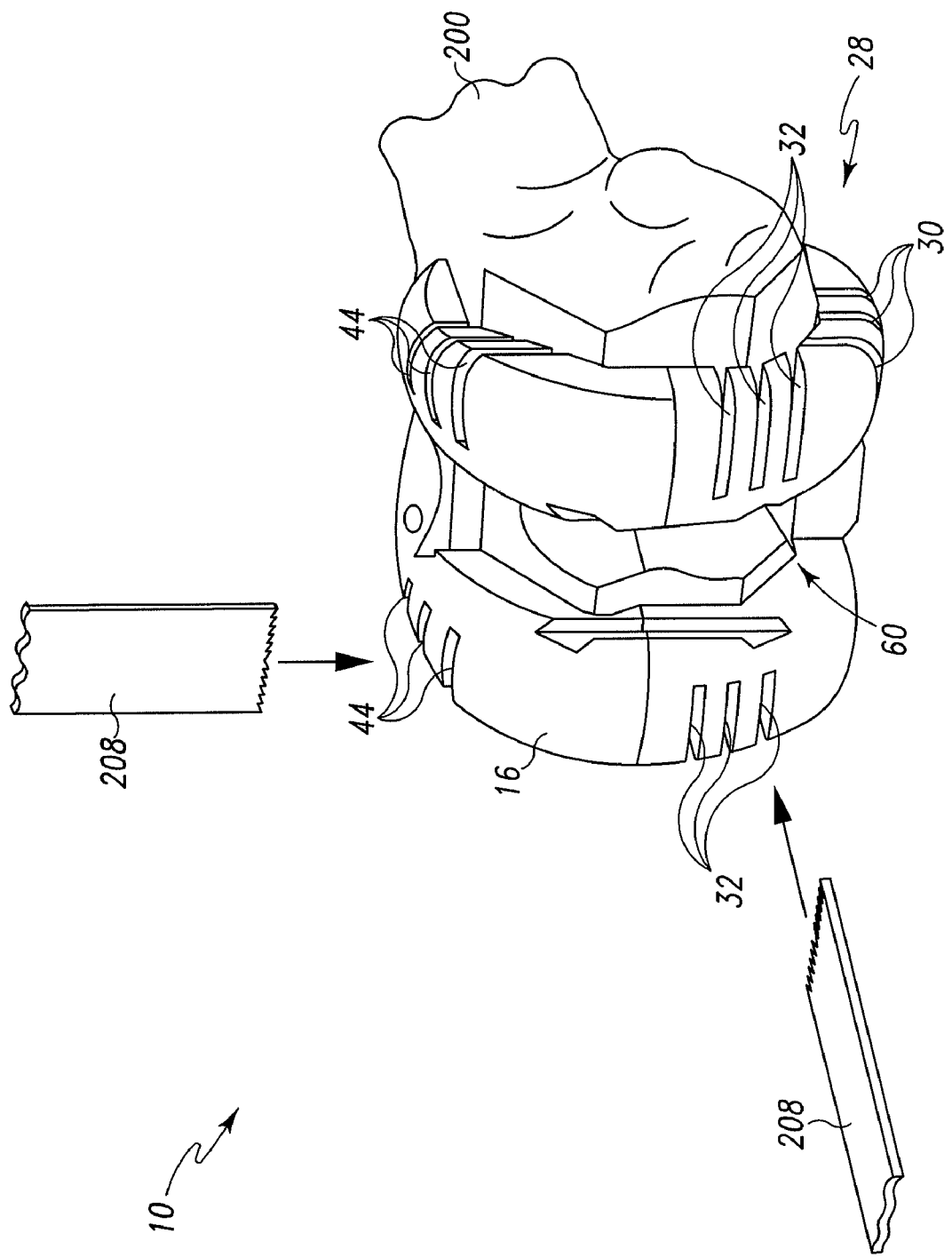
FIG. 5 is a perspective view of another configuration of the modular femoral orthopaedic surgical instrument of FIG. 1 coupled to a femur of a patient.

After the surgeon has performed the anterior resection of the patient's femur 200, the surgeon may use the instrument 10 to perform additional resectioning. For example, in process step 120, the orthopaedic surgeon uses the instrument 10 for augment resectioning of the patient's femur 200. To do so, in process step 122, the instrument 10 is assembled in a configuration for augment resectioning. That is, as illustrated in FIG. 5, the base block 82 is removed from the posterior femoral trial 14. The anterior femoral trial 16 is coupled to the posterior femoral trial 14 in place of the base block 82. As discussed above, the trials 14, 16 may be coupled together using pins, screws, bolts, or the like. Additionally, when the trials 14, 16 are coupled together, the individual openings 26, 40 of each trial 14, 16 form an opening 60 as illustrated in FIG. 5.

After the instrument 10 has been assembled for in the augment resectioning configuration, the surgeon may perform the augment resectioning in process step 124. To do so, as shown in FIG. 5, the surgeon may use the cutting guides 28, 42 of the trials 14, 16. For example, the surgeon may perform the augment resection by inserting the bone saw blade into one of the posterior cutting guides 32 of the posterior femoral trial 14. Additionally or alternatively, the surgeon may insert the bone saw blade 208 into one of the distal cutting guides 44 of the anterior femoral trial 16. The surgeon may use the instrument 10 to perform any amount of augment resectioning. In addition, because the anterior femoral trial 16 is being used, the instrument 10 may be used for further balancing of the flexion and extension gaps. As such, it should be appreciated that the instrument 10 may be used for balancing as well as resectioning of the patient's femur 200 and joint.

Figure 6:
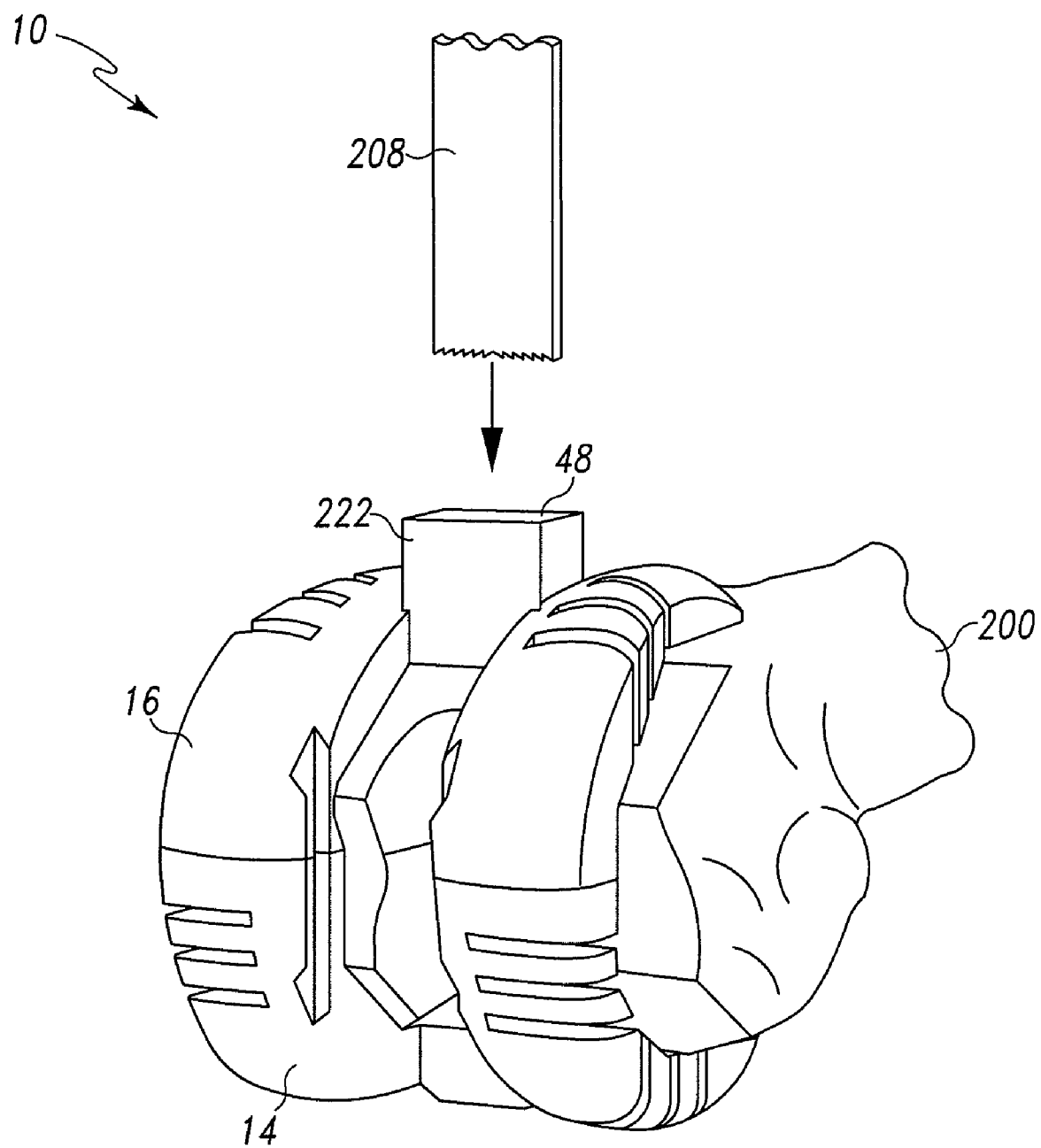
FIG. 6 is a perspective view of another configuration of the modular femoral orthopaedic surgical instrument of FIG. 1 coupled to a femur of a patient.

In addition to the augment cuts performed in process step 120, the instrument 10 may be used to perform a number of femoral box cuts in process 126. To do so, the instrument 10 is assembled into a configuration for the femoral box cuts. That is, as illustrated in FIG. 6, the box cut guide 48 is coupled to the anterior femoral trial 16. As discussed above in regard to FIG. 1, the box cut guide 48 may be coupled to the trial 16 by position the guide 48 such that the pegs 52 of the guide 48 are received in the apertures 46 defined in the articulating surface 34 of the anterior femoral trial 16.

After the box cut guide 48 has been coupled to the anterior femoral trial 16, the orthopaedic surgeon may perform the femoral box cuts in process step 130. To do so, the surgeon uses the top surface 212 of the box cut guide 48 to guide the bone saw blade 208. Again, the bone saw blade 208 is typically kept substantially flat on the surface 212 to perform the box cut. The femoral box cut removes portions of the patient's femur 200 to define an area for the femoral box of the femoral orthopaedic prosthesis.

Figure 7:
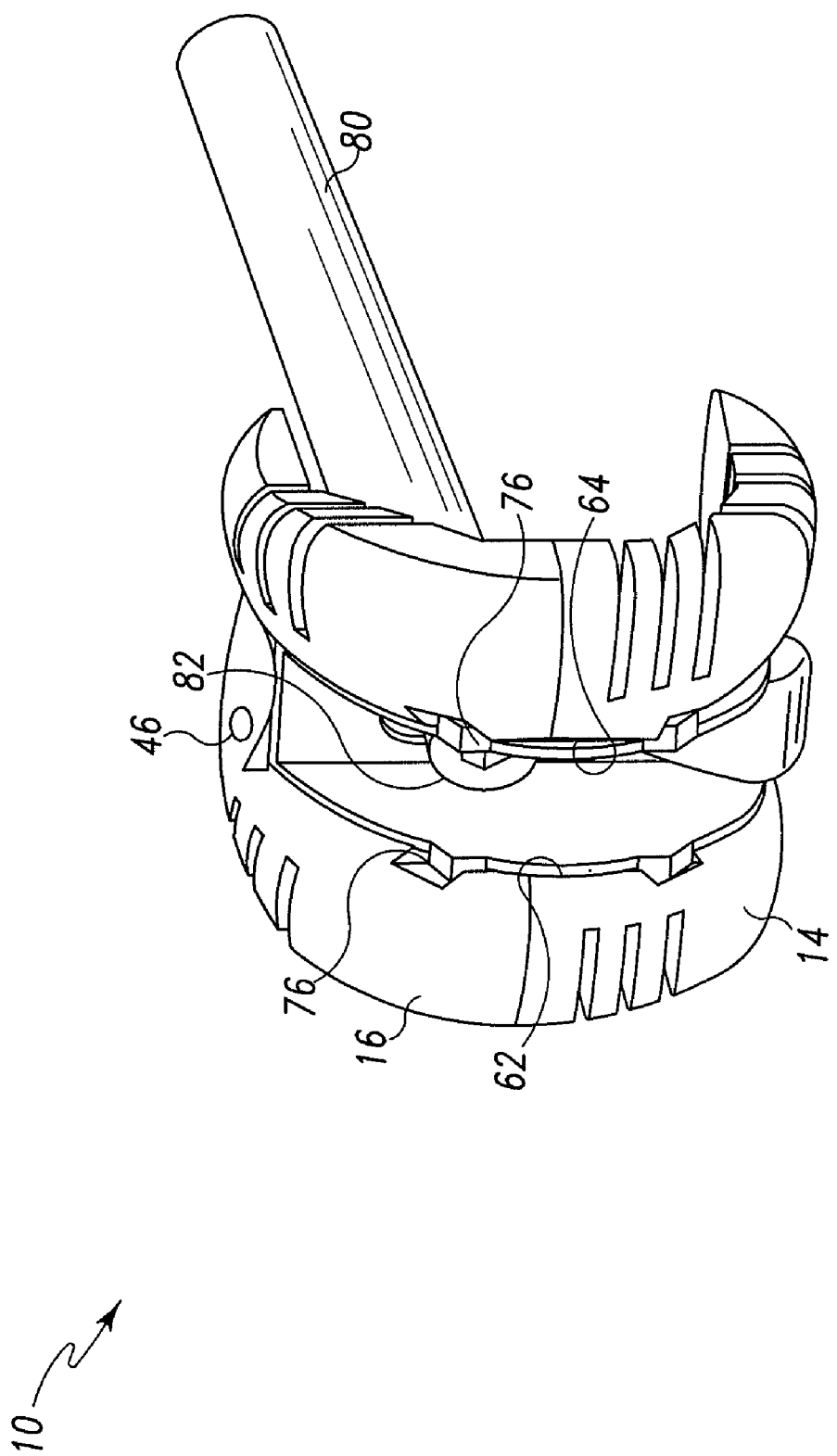
FIG. 7 is a perspective view of another configuration of the modular femoral orthopaedic surgical instrument of FIG. 1.

After the orthopaedic surgeon has resectioned the patient's femur as desired, the surgeon may use the instrument 10 as a femoral trial to balance the patient's knee joint. To do so, the instrument 10 is assembled in a femoral trial configuration as illustrated in FIG. 7. That is, the femoral box trial 18 is coupled to the anterior femoral trial 16 and the posterior femoral trial 14. As discussed above, the femoral box trial 18 may be coupled to the posterior and anterior trials 14, 16 by positioning the femoral box trial 18 such that the rails 74, 76 of the femoral box trial 18 are received in the corresponding tracks 62, 64 of the trials 14, 16. The stem 80 may be secured to the femoral box trial 18 using the bolt 82. It should be appreciated that the stem 80 is received in prepared intramedullary canal of the femur 200 (not shown for clarity of description).

After the instrument 10 has been assembled for trials, the orthopaedic surgeon may analyze the patient's joint using the instrument 10. For example, the surgeon may analyze the joint gap between the patient's femur 200 and tibia. Once satisfied with the preparation of the patient's femur, the orthopaedic surgeon may remove the instrument 10 from the femur 200 and implant the femoral prosthesis component.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the devices and methods described herein. It will be noted that alternative embodiments of the devices and methods of the present disclosure may not include all of the features described yet still benefit from at least some of the advantages of such features. Those of ordinary skill in the art may readily devise their own implementations of the devices and methods that incorporate one or more of the features of the present invention and fall within the spirit and scope of the present disclosure as defined by the appended claims.

The invention claimed is:

1. A femoral orthopaedic surgical instrument comprising:
    a posterior femoral trial including a cutting guide defined therein;
    a base block removably coupled to the posterior femoral trial and configured to be coupled to a femur of a patient, the base block including an opening;
    a bushing coupled to the base block and received in the opening, the bushing having an aperture defined therethrough configured to receive an orthopaedic surgical instrument; and
    an anterior femoral trial including a cutting guide defined therein, wherein the anterior femoral trial is configured to be coupled to the posterior femoral trial in place of the base block,
    wherein the bushing comprises (i) a frame received in the opening of the base block and (ii) a bushing insert received in the frame, the bushing insert having an aperture defined therein configured to receive an orthopaedic surgical instrument.

2. The femoral orthopaedic surgical instrument of claim 1, wherein the posterior femoral trial includes a first cutting guide, a second cutting guide spaced from the first cutting guide by a first distance, and a third cutting guide spaced from the second cutting guide by the first distance.

3. The femoral orthopaedic surgical instrument of claim 1, wherein the posterior femoral trial includes a distal cutting guide and a posterior cutting guide.

4. The femoral orthopaedic surgical instrument of claim 1, further comprising an intramedullary rod received in the aperture of the bushing.

5. The femoral orthopaedic surgical instrument of claim 1, further comprising a stylus coupled to the base block.

6. The femoral orthopaedic surgical instrument of claim 1, further comprising a box cutting guide coupled to the anterior femoral trial, the box cutting guide comprises a platform, a first peg extending from the platform, and a second peg extending from the platform,
    wherein the anterior femoral trial includes a first aperture and a second aperture, the first peg being received in the first aperture and the second peg being received in the second aperture.

7. The femoral orthopaedic surgical instrument of claim 1, further comprising a femoral box trial configured to be coupled to the anterior femoral trial and the posterior femoral trial.

8. The femoral orthopaedic surgical instrument of claim 7, wherein:
    (i) the anterior femoral trial includes a first slot and second slot,
    (ii) the posterior femoral trial includes a third slot and fourth slot, and
    (iii) the femoral box trial includes a first rail and a second rail, the first rail being received in the first slot and the third slot and the second rail being received in the second slot and the fourth slot when the femoral box trial is coupled to the anterior femoral trial and the posterior femoral trial.

9. The femoral orthopaedic surgical instrument of claim 7, wherein the femoral anterior trial and the femoral posterior trial define an aperture therebetween when coupled together, the femoral box trial being received in the aperture.

10. The femoral orthopaedic surgical instrument of claim 7, further comprising a stem configured to be coupled to the femoral box trial.

11. A modular femoral trial comprising:
a posterior femoral trial including a first cutting guide defined therein;
an anterior femoral trial separate from the posterior femoral trial and removably coupled thereto, the anterior femoral trial including a second cutting guide defined therein;
a base block configured to be coupled to the posterior femoral trial in place of the anterior femoral trial, the base block including a plurality of guide pin apertures; and
a box cutting guide coupled to the anterior femoral trial, the box cutting guide having a first peg and a second peg,
wherein the anterior femoral trial includes a first aperture and a second aperture, the first peg being received in the first aperture and the second peg being received in the second aperture.

12. The modular femoral trial of claim 11, further comprising a femoral box trial coupled to the anterior femoral trial and the posterior femoral trial.

13. The modular femoral trial of claim 12, wherein the femoral anterior trial and the femoral posterior trial define an aperture therebetween, the femoral box trial being received in the aperture.

14. The modular femoral trial of claim 12, wherein:
(i) the anterior femoral trial includes a first slot and second slot,
(ii) the posterior femoral trial includes a third slot an fourth slot, and
(iii) the femoral box trial includes a first rail received in the first slot and the third slot and a second rail received in the second slot and the fourth slot.

15. The modular femoral trial of claim 11, wherein the posterior femoral trial includes a distal cutting guide and a posterior cutting guide.

16. An method for performing an orthopaedic surgical procedure, the method comprising:
coupling a posterior femoral trial having a cutting guide defined therein with a base block;
securing the base block to a patient's femur;
resectioning the patient's femur using the cutting guide of the posterior femoral trial;
removing the base block from the posterior femoral trial;
coupling an anterior femoral trial having a cutting guide to the posterior femoral trial; and
resectioning the patient's femur using the cutting guide of the anterior femoral trial.

* * * * *